United States Patent
Prevost et al.

(10) Patent No.: US 6,544,995 B1
(45) Date of Patent: Apr. 8, 2003

(54) USE OF CYSTEINE DERIVATIVES FOR PREPARING A MEDICINE FOR TREATING PATHOLOGIES RESULTING FROM THE FORMATION OF HETEROTRIMERIC G PROTEIN

(75) Inventors: Grégoire Prevost, Antony (FR); Marie-Odile Lonchampt, Chevilly-Larue (FR); Thomas Gordon, Medway, MA (US)

(73) Assignee: Societe de Conseils de Recherches et d'Applications Scientifiques (S.C.R.A.S.) (FR)

( * ) Notice: Subject to any disclaimer, the term of this patent is extended or adjusted under 35 U.S.C. 154(b) by 0 days.

(21) Appl. No.: 09/743,208

(22) PCT Filed: Jul. 5, 1999

(86) PCT No.: PCT/FR99/01609

§ 371 (c)(1),
(2), (4) Date: Jan. 4, 2001

(87) PCT Pub. No.: WO00/02881

PCT Pub. Date: Jan. 20, 2000

(30) Foreign Application Priority Data

Jul. 8, 1998 (FR) ............................................. 98 08731

(51) Int. Cl.[7] .................... C07D 487/04; A61K 31/519; A61P 3/04
(52) U.S. Cl. ....................................... 514/249; 544/350
(58) Field of Search ........................... 514/249; 544/350

(56) References Cited

U.S. PATENT DOCUMENTS 6,001,553 A * 12/1999 Broach et al. .............. 435/232

FOREIGN PATENT DOCUMENTS

WO    WO 97/30053 A1 * 8/1997

OTHER PUBLICATIONS

Holler C, Freissmuth M, Nanoff C., "G proteins as a drug targets.", Cell Mol Life Sci. 1999 Feb.;55(2):257–70, Medline Abstract.*

* cited by examiner

Primary Examiner—Mukund J. Shah
Assistant Examiner—Thomas McKenzie
(74) Attorney, Agent, or Firm—Bierman, Muserlian and Lucas (57) ABSTRACT

The invention relates to the use of cysteine derivatives for preparing a medicament intended to treat diseases which result from the formation of the heterotrimeric G protein. These diseases include in particular diseases linked to the following biological functions or disorders: smell, taste, perception of the light, neurotransmission, neurodegeneration, endocrine and exocrine gland functions, autocrine and paracrine regulation, arterial tension, embroygenesis, benign cell proliferation, oncogenesis, viral infection, immunological functions, diabetes, obesity, and benign and malign proliferative diseases.

Said cysteine derivatives include in particular:
bis-1,1'-[7-(2-amino-1-oxo-3-thiopropyl)-8-(cyclohexylmethyl)-2-(2-methoxyphenyl)-5,6,7,8-tetrahydroimidazo[1.2a]pyrazine disulphide (I), and
bis-1,1'-7-(2-amino-1-oxo-3-thiopropyl-(2-(1-naphtyl)-8-(2-methylpropyl)-5,6,7,8-tetrahydroimidazo[1.2a]pyrazin-7-yl)disulphide (II).

6 Claims, 4 Drawing Sheets

USE OF CYSTEINE DERIVATIVES FOR PREPARING A MEDICINE FOR TREATING PATHOLOGIES RESULTING FROM THE FORMATION OF HETEROTRIMERIC G PROTEIN

This application is a 371 of PCT/FR99/01609 filed Jul. 5, 1999.

The present invention relates in particular to the use of derivatives of cysteine for the preparation of a medicament intended to treat pathologies which result from the formation of the heterotrimeric G protein. These diseases include in particular diseases linked to the following biological functions or disorders: smell, taste, perception of light, neurotransmission, neurodegeneration, endocrine and exocrine gland functions, autocrine and paracrine regulation, arterial tension, embryogenesis, benign cell proliferation, oncogenesis, viral infection, immunological functions, diabetes, obesity, and benign and malign proliferative diseases.

The G proteins are in fact the structural association of three distinct sub-units called α, β and γ, but operate as dissociable entities constituted by α sub-units on the one hand and β/γ dimers on the other hand.

The G proteins participate in the transmission of signals outside the cell thanks to its interaction with receptors with seven transmembrane domains inside using different effectors including adenylate cyclase, phospholipase C or also the ionic channels. The adenylate cyclase enzyme generates cyclic AMP (cAMP) (cf. Gilman, A. G. *Biosci. Rep.* 15, 65–97 (1995)). Thus, it is known that, in order to activate the adenylate cyclase, it is necessary for the G proteins to be transitionally in a heterotrimeric form, in which form the monomer constituted by an α sub-unit is associated with the dimer constituted by the β and γ sub-units. It is only in this situation that the signal outside the cell can activate the a sub-unit of α G protein, which can, after disassociation, modulate the adenylate cyclase and modulate the production of cAMP.

It is also known that the β/γ dimers can directly activate the effectors leading to the activation of kinases regulated by extracellular signals (ERKs) or MAP kinases. A direct link between the β/γ sub-units and the src or src like kinases has been demonstrated (cf. Gutkind, J. S. *J.Biol.Chem.* 273, 1839–1842 (1998)).

Moreover, bacterial toxins such as *Vibrio cholera* and *Bortella pertussis*, peptides such as mastoparan and suramin have been presented as directly modulating the activity of the G proteins (cf. Freissmuth, M., Boehm, S., Beindl, W., et al. *Mol.Pharmacol.* 49, 602–611 (1996); Boehm, S., Huck, S., Motejlek, A., et al. *Journal of Neurochemistry* 66, 1019–1026 (1996); Cachero, T. G., Rigual, R., Rocher, A. & Gonzalez, C. *Eur.J.Neurosci.* 8, 2320–2327 (1996); Danilenko, M., Worland, P., Carlson, B., Sausville, E. A. & Sharoni, Y. *Biochem. Biophys. Res. Commun.* 196, 1296–1302 (1993); Beindl, W., Mitterauer, T., Hohenegger, M., Ijzerman, A. P., Nanoff, C. & Freissmuth, M. *Mol. Pharmacol.* 50, 415–423 (1996)).

For example, the choleric toxin modifies the $\alpha_S$ sub-unit of the G protein by adding an ADP-ribose originating from the NAD to an arginine-specific acceptor site. This completely blocks the activity of the GTPase, provoking persistent stimulation of its next effector, adenylate cyclase and leading to overproduction of cAMP.

The harmful effects of an abnormal cAMP level are also known and occur in particular at the level of the following biological functions or disorders: smell, taste, perception of light, neurotransmission, neurodegeneration, endocrine and exocrine gland functions, autocrine and paracrine regulation, arterial tension, embryogenesis, benign cell proliferation, oncogenesis, viral infection and immunological functions, diabetes and obesity.

The Applicant has just discovered that certain derivatives of cysteine, namely the compounds of general formula (A)

(A)

corresponding to sub-formulae (A1) or (A2):

(A1)

(A2)

in which:

X represents $R_{12}$ and Y represents $R_8$, or X and Y complete a ring with 6 members, the X-Y set representing the —CH($R_8$)—CH($R_9$)— radical;

$R_1$ represents H, a lower alkyl or alkylthio radical;

$R_2$ and $R_3$ represent independently H or a lower alkyl radical;

$R_4$ represents $H_2$ or O;

$R_5$ represents H, or one of the lower alkyl, lower alkenyl, lower alkynyl, aryl, lower arylalkyl, heterocycle or lower alkyl heterocycle radicals, these radicals being optionally substituted by radicals chosen from the group comprising a lower alkyl radical, —O—$R_{10}$, —S(O)$_m$$R_{10}$ (m representing 0, 1, or 2), —N($R_{10}$)($R_{11}$), —N—C(O)—$R_{10}$, —NH—(SO$_2$)—$R_{10}$, —CO$_2$—$R_{10}$, C(O)—N($R_{10}$)($R_{11}$), and —(SO$_2$)—N($R_{10}$)($R_{11}$);

$R_6$ and $R_7$ represent independently H, a —C(O)—NH—CHR$_{13}$—CO$_2$R$_{14}$ radical, or one of the lower alkyl, aryl, lower arylalkyl, heterocycle or lower alkyl heterocycle radicals, these radicals being optionally substituted by radicals chosen from the group comprising the OH, alkyl or lower alkoxy, N($R_{10}$)($R_{11}$), COOH, CON($R_{10}$)($R_{11}$), and halo radicals, or $R_6$ and $R_7$ form together an aryl radical or a heterocycle;

$R_8$ and $R_9$ represent independently, H, or one of the lower alkyl, aryl, lower arylalkyl, heterocycle or lower alkyl heterocycle radicals, these radicals being optionally substituted by radicals chosen from the group comprising the OH, alkyl or lower alkoxy, N($R_{10}$)($R_{11}$), COOH, CON($R_{10}$)($R_{11}$) and halo radicals, or $R_8$ and $R_9$ together form an aryl radical or a heterocycle;

$R_{10}$ and $R_{11}$ represent independently H, an aryl radical or a heterocycle, or an alkyl, arylalkyl or lower alkyl heterocycle radical;

$R_{12}$ represents $NR_9$, S, or O;

$R_{13}$ represents a lower alkyl radical optionally substituted by a radical chosen from the lower alkyl, —$OR_{10}$, —$S(O)_m R_{10}$ (m representing 0, 1, or 2) and —$N(R_{10})(R_{11})$ radicals;

$R_{14}$ represents H or a lower alkyl radical;

or the compounds of general formula (B):

$$W_1-Ar-W_2 \quad (B)$$

in which:

$W_1$ represents a remainder originating from a cysteine in reduced or non reduced form;

Ar represents a radical derived from an aminobenzoic acid, the aromatic ring of which is optionally substituted;

$W_2$ represents an amino acid, preferably an aliphatic amino acid;

or also the compounds of general formula (C):

(C)

in which:

$Z_1$ represents a lower alkyl radical;

$Z_2$ and $Z_3$ both represent H or $Z_2$ and $Z_3$ together form a chain having 2 to 4 elements chosen from the —C(O)—, —$CH_2$—, —$CH(NH_2)$— and —S— radicals, it being understood that two successive elements are not both —C(O)—;

it being understood that the compounds of general formula (C) can also be presented in the form of dimers, when the $Z_2$ radical represents a hydrogen atom which can be eliminated by oxidization;

or also a pharmaceutically acceptable salt of a compound of general formula (A), (B) or (C);

can be used to prepare medicaments intended to treat pathologies which result from the formation of the heterotrimeric G protein.

By lower alkyl radical, is understood a linear or branched alkyl radical containing 1 to 6 carbon atoms, and in particular the methyl, ethyl, propyl, isopropyl, butyl, isobutyl, sec-butyl and tert-butyl, pentyl, neopentyl, isopentyl, hexyl, isohexyl radicals. By heterocycle radical is understood a radical constituted by one or more rings and including at least one heteroatom. By arylalkyl, alkyl heterocycle, alkylthio or lower alkoxy radical, is understood the radicals of which the alkyl radical has the meaning indicated previously.

Preferably, the Ar radical included in formula (B) is optionally substituted by an alkyl radical comprising 1 to 6 carbon atoms or an aryl radical, these alkyl or aryl radicals themselves being optionally substituted preferentially by an alkoxy radical having 1 to 4 carbon atoms, fluoro, chloro, bromo. The aryl radical preferably a phenyl can itself be substituted by an alkyl radical.

Preferably also, the compounds of general formula (B) are such that Ar represents a radical derived from an aminobenzoic acid the aromatic ring of which is substituted by a phenyl radical and $W_2$ represents an aliphatic amino acid.

In particular, the following compounds can be used to prepare medicaments intended to treat pathologies which result from the formation of the heterotrimeric G protein:

7-(2-amino-1-oxo-3-thiopropyl)-8-(cyclohexylmethyl)-2-(2-methylphenyl)-5,6,7,8-tetrahydroimidazo[1.2a]pyrazine;

7-(2-amino-1-oxo-3-thiopropyl)-8-butyl-2-(2-methoxyphenyl)-5,6,7,8-tetrahydroimidazo[1.2a]pyrazine;

7-(2-amino-1-oxo-3-thiopropyl)-8-(1-methylpropyl)-2-(2-methoxyphenyl)-5,6,7,8-tetrahydroimidazo[1.2a]pyrazine;

1-[2(R)-amino-3-mercaptopropyl]-2(S)-n-butyl-4-(1-naphthoyl)piperazine;

bis-1,1'-[7-(2-amino-1-oxo-3-thiopropyl)-2-(methoxyphenyl)-8-(1-methylpropyl)-5,6,7,8-tetrahydroimidazo[1.2a]pyrazine]disulphide;

bis-1,1'-[7-(2-amino-1-oxo-3-thiopropyl)-8-(cyclohexylmethyl)-2-(2-methoxyphenyl)-5,6,7,8-tetrahydroimidazo[1.2a]pyrazine disulphide;

bis-1,1'-7-(2-amino-1-oxo-3-thiopropyl-(2-(1-naphthyl)-8-(2-methylpropyl)-5,6,7,8-tetrahydroimidazo[1.2a]pyrazin-7-yl)disulphide;

the compound of formula:

(VII)

the compound of formula:

7-(2-amino-1-oxo-3-thiopropyl)-8-(cyclohexylmethyl)-2-phenyl-5,6,7,8-tetrahydroimidazo[1.2a]pyrazine;

7-(2-amino-1-oxo-3-thiopropyl)-2-(2-methoxyphenyl)-8-(phenylmethoxy)methyl-5,6,7,8-tetrahydroimidazo[1.2a]pyrazine;

7-(2-amino-1-oxo-3-thiopropyl)-2-(2-methoxyphenyl)-8-(1-phenylmethoxy)ethyl-5,6,7,8-tetrahydroimidazo[1.2a]pyrazine;

7-(2-amino-1-oxo-3-thiopropyl)-2-(2-methoxyphenyl)-8-(phenoxyethyl)-5,6,7,8-tetrahydroimidazo[1.2a]pyrazine;

7-(2-amino-1-oxo-3-thiopropyl)-2-(2-methyoxyphenyl)-8-(phenoxyethyl)-5,6,7,8-tetrahydro-imidazo[1.2a]pyrazine, or its dimeric form;

and 7-(2-amino-1-oxo-3-thiopropyl)-2-(2-methoxyphenyl)-8-(phenylsulphonylethyl)-5,6,7,8-tetrahydro-imidazo[1.2a]pyrazine;

or also a pharmaceutically acceptable salt of one of these compounds.

One of the following compounds is preferably used for the invention:

bis-1,1'-[7-(2-amino-1-oxo-3-thiopropyl)-8-(cyclohexylmethyl)-2-(2-methoxyphenyl)-5,6,7,8-tetrahydroimidazo[1.2a]pyrazine disulphide (I);

bis-1,1'-7-(2-amino-1-oxo-3-thiopropyl-(2-(1-naphthyl)-8-(2-methylpropyl)-5,6,7,8-tetrahydroimidazo[1.2a]pyrazin-7-yl)disulphide (II);

7-(2-amino-1-oxo-3-thiopropyl)-8-(cyclohexylmethyl)-2-(2-methylphenyl)-5,6,7,8-tetrahydroimidazo[1.2a]pyrazine (III);

the compound of formula:

(IV)

7-(2-amino-1-oxo-3-thiopropyl)-8-butyl-2-(2-methoxyphenyl)-5,6,7,8-tetrahydroimidazo[1.2a]pyrazine (V);

bis-1,1'-[7-(2-amino-1-oxo-3-thiopropyl)-2-(methoxyphenyl)-8-(1-methylpropyl)-5,6,7,8-tetrahydroimidazo[1.2a]pyrazine]disulphide (VI);

the compound of formula:

(VII)

7-(2-amino-1-oxo-3-thiopropyl)-8-(cyclohexylmethyl)-2-phenyl-5,6,7,8-tetrahydroimidazo[1.2a]pyrazine;

7-(2-amino-1-oxo-3-thiopropyl)-8-(1-methylpropyl)-2-(2-methoxyphenyl)-5,6,7,8-tetrahydroimidazo[1.2a]pyrazine;

1-[2(R)-amino-3-mercaptopropyl]-2(S)-n-butyl-4-(1-naphthoyl)piperazine;

or a pharmaceutically acceptable salt of one of the latter.

More preferentially, one of the following compounds is used for the invention:

bis-1,1'-[7-(2-amino-1-oxo-3-thiopropyl)-8-(cyclohexylmethyl)-2-(2-methoxyphenyl)-5,6,7,8-tetrahydroimidazo[1.2a]pyrazine disulphide (I);

bis-1,1'-7-(2-amino-1-oxo-3-thiopropyl-(2-(1-naphthyl)-8-(2-methylpropyl)-5,6,7,8-tetrahydroimidazo[1.2a]pyrazin-7-yl)disulphide (II);

7-(2-amino-1-oxo-3-thiopropyl)-8-(cyclohexylmethyl)-2-(2-methylphenyl)-5,6,7,8-tetrahydroimidazo[1.2a]pyrazine (III);

7-(2-amino-1-oxo-3-thiopropyl)-8-butyl-2-(2-methoxyphenyl)-5,6,7,8-tetrahydroimidazo[1.2a]pyrazine (V);

the compound of formula:

(VII)

or a pharmaceutically acceptable salt of one of the latter.

Finally, the following compounds are more particularly preferred:

bis-1,1'-[7-(2-amino-1-oxo-3-thiopropyl)-8-(cyclohexylmethyl)-2-(2-methoxyphenyl)-5,6,7,8-tetrahydroimidazo[1.2a]pyrazine disulphide (I);

bis-1,1'-7-(2-amino-1-oxo-3-thiopropyl-(2-(1-naphthyl)-8-(2-methylpropyl)-5,6,7,8-tetrahydroimidazo[1.2a]pyrazin-7-yl)disulphide (II);

or a pharmaceutically acceptable salt of one of the latter.

The invention therefore relates firstly to the use of the compounds of general formula (A), (B) or (C) as described previously for preparing a medicament intended to treat pathologies which result from the formation of the heterotrimeric G protein. In particular, it relates to the use of said inhibitors for preparing medicaments intended to treat diseases linked to the following biological functions or disorders: smell, taste, perception of light, neurotransmission, neurodegeneration, endocrine and exocrine gland functions, autocrine and paracrine regulation, arterial tension, embryogenesis, viral infection, immunological functions, diabetes and obesity.

More particularly, the invention relates to the use of compounds of general formula (A), (B) or (C) for preparing a medicament intended to treat cholera, Acquired Immune Deficiency Syndrome (AIDS), travel diarrhea and familial masculine precocious puberty.

A subject of the invention is also new products of general formula (A) numbered 1 to 7 and described hereafter in the examples, namely:

7-(2-amino-1-oxo-3-thiopropyl)-8-(cyclohexylmethyl)-2-(2-methylphenyl)-5,6,7,8-tetrahydroimidazo[1.2a]pyrazine;

7-(2-amino-1-oxo-3-thiopropyl)-8-(cyclohexylmethyl)-2-phenyl-5,6,7,8-tetrahydroimidazo[1.2a]pyrazine;

7-(2-amino-1-oxo-3-thiopropyl)-2-(2-methoxyphenyl)-8-(phenylmethoxy)methyl-5,6,7,8-tetrahydroimidazo[1.2a]pyrazine;

7-(2-amino-1-oxo-3-thiopropyl)-2-(2-methoxyphenyl)-8-(1-phenylmethoxy)ethyl-5,6,7,8-tetrahydroimidazo[1.2a]pyrazine;
7-(2-amino-1-oxo-3-thiopropyl)-2-(2-methoxyphenyl)-8-(phenoxyethyl)-5,6,7,8-tetrahydroimidazo[1.2a]pyrazine;
7-(2-amino-1-oxo-3-thiopropyl)-2-(2-methyoxyphenyl)-8-(phenoxyethyl)-5,6,7,8-tetrahydro-imidazo[1.2a]pyrazine, or its dimeric form;
and 7-(2-amino-1-oxo-3-thiopropyl)-2-(2-methoxyphenyl)-8-(phenylsulphonylethyl)-5,6,7,8-tetrahydro-imidazo[1.2a]pyrazine.

A subject of the invention is also said new products or their pharmaceutically acceptable salts as medicaments, as well as their use for preparing a medicament intended to treat pathologies which result from the formation of the heterotrimeric G protein. In particular, it relates to the use of said products for preparing medicaments intended to treat diseases linked to the following biological functions or disorders: smell, taste, perception of light, neurotransmission, neurodegeneration, endocrine and exocrine gland functions, autocrine and paracrine regulation, arterial tension, embryogenesis, benign cell proliferation, oncogenesis, viral infection, immunological functions, diabetes, obesity, and benign and malign proliferative diseases.

The products particularly preferred for use according to the invention are therefore the following:
bis-1,1'-[7-(2-amino-1-oxo-3-thiopropyl)-8-(cyclohexylmethyl)-2-(2-methoxyphenyl)-5,6,7,8-tetrahydroimidazo[1.2a]pyrazine disulphide;
bis-1,1'-7-(2-amino-1-oxo-3-thiopropyl-(2-(1-naphthyl)-8-(2-methylpropyl)-5,6,7,8-tetrahydroimidazo[1.2a]pyrazin-7-yl)disulphide;
the compound of formula:

7-(2-amino-1-oxo-3-thiopropyl)-8-(cyclohexylmethyl)-2-(2-methylphenyl)-5,6,7,8-tetrahydroimidazo[1.2a]pyrazine;
7-(2-amino-1-oxo-3-thiopropyl)-8-(cyclohexylmethyl)-2-phenyl-5,6,7,8-tetrahydroimidazo[1.2a]pyrazine;
7-(2-amino-1-oxo-3-thiopropyl)-2-(2-methoxyphenyl)-8-(phenylmethoxy)methyl-5,6,7,8-tetrahydroimidazo[1.2a]pyrazine;
7-(2-amino-1-oxo-3-thiopropyl)-2-(2-methoxyphenyl)-8-(1-phenylmethoxy)ethyl-5,6,7,8-tetrahydroimidazo[1.2a]pyrazine;
7-(2-amino-1-oxo-3-thiopropyl)-2-(2-methoxyphenyl)-8-(phenoxyethyl)-5,6,7,8-tetrahydroimidazo[1.2a]pyrazine;
7-(2-amino-1-oxo-3-thiopropyl)-2-(2-methyoxyphenyl)-8-(phenoxyethyl)-5,6,7,8-tetrahydroimidazo[1.2a]pyrazine, or its dimeric form;
and 7-(2-amino-1-oxo-3-thiopropyl)-2-(2-methoxyphenyl)-8-(phenylsulphonylethyl)-5,6,7,8-tetrahydroimidazo[1.2a]pyrazine;

or a pharmaceutically acceptable salt of one of the latter.

Similarly, the invention relates more particularly to the use of the compounds previously mentioned for preparing a medicament intended to treat cholera, Acquired Immune Deficiency Syndrome (AIDS), travel diarrhea and familial masculine precocious puberty.

The compounds of general formula (A) and their preparation are described in the Patent Application WO 97/30053 or in the examples hereafter. The compounds of general formula (B) and their preparation are described in the Patent Application WO 96/21456. Finally, the preparation of the compounds of general formula (C) is described in the Patent Application PCT WO 95/00497, except for the compound of formula (VII) for which the synthesis is described in the experimental part of this Application.

The pharmaceutical compositions comprising a compound of the invention can be in the form of solids, for example powders, granules, tablets, gelatin capsules, liposomes or suppositories. The appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions comprising a compound of the invention can also be presented in liquid form, for example, solutions, emulsions, suspensions or syrups. The appropriate liquid supports can be, for example, water, organic solvents such as glycerol or glycols, as well as their mixtures, in varying proportions, in water.

The administration of a medicament according to the invention can be carried out by topical, oral, parenteral route, by injection (intramuscular, sub-cutaneous, intravenous, etc.), etc. The administration route will of course depend on the type of disease to be treated.

The administration dose envisaged for a medicament according to the invention is comprised between 0.1 mg and 10 g depending on the type of pathology to be treated.

Unless they are defined in another manner, all the technical and scientific terms used here have the same meaning as that usually understood by an ordinary specialist in the field to which this invention belongs. Similarly, all the publications, patent applications, all the patents and all other references mentioned here are incorporated by way of reference.

EXAMPLES

Example 1

7-(2-amino-1-oxo-3-thiopropyl)-8-(cyclohexylmethyl)-2-(2-methylphenyl)-5,6,7,8-tetrahydroimidazo[1.2a]pyrazine: 1

Compound 1 was prepared according to the synthesis diagram below:

Diagram 1

1.a) Carbobenzyloxy-L-cyclohexylalanine

L-phenylalanine (10.0 g; 60.6 mmol) is combined with PtO2 (430 mg) in acetic acid (60 ml) and the mixture is hydrogenated overnight under 20–50 psi $H_2$. A 5% aqueous solution of HCl is added to the mixture in order to obtain a limpid solution and hydrogenation is continued until the consumption of hydrogen ceases. The catalyst is eliminated by filtration and the filtrate is concentrated under reduced pressure. The residue is taken up in methanol and water and the pH is adjusted to 4.4 by the addition of a 10% solution of NaOH. The product obtained is recovered by filtration and used without further purification.

L-cyclohexylalanine (60.6 mmol) is suspended in water (100 ml), $K_2CO_3$ (8.36 g; 60.6 mmol) is added, then a solution of N-(benzyloxycarbonyloxy)succinimide (15.1 g; 60.6 mmol) in $CH_3CN$ (150 ml) and the mixture obtained is agitated vigorously for 45 minutes. The mixture is concentrated in order to produce a volume of approximately 100 ml and washed with $Et_2O$ (100 ml), then acidified with concentrated HCl and extracted with AcOEt (2×50 ml). The combined AcOEt phases are dried over $Na_2SO_4$, filtered and concentrated in order to produce a clear oil (17.27 g; 93%).

NMR $^1H$ (DMSO-d6): 7.5–7.6 (1H, d); 7.2–7.5 (5H, m); 5.0–5.1 (2H, s); 3.9–4.1 (1H, m); 0.7–1.8 (13H, m).

1.b) 2-(1-(S)-((phenylmethoxy)carbonyl)-amino-2-(cyclohexyl)methyl)-4-(2-methylphenyl)-imidazole Cbz-(L)-cyclohexylalanine (4.58 g; 15.0 mmol) and $Cs_2CO_3$ (2.44 g; 7.50 mmol) are placed in a 2:1 mixture of $DMF:H_2O$ (75 ml). The mixture obtained is agitated until it becomes homogeneous. The solvents are eliminated under reduced pressure, the residue is dissolved in DMF (60 ml) and 2-bromo-2'-methylacetophenone (3.20 g; 15.0 mmol) in DMF (30 ml) is added. The mixture is agitated overnight at ambient temperature then filtered and concentrated under reduced pressure. The keto-ester obtained is solubilized in xylenes (100 ml) and ammonium acetate (19.5 g; 0.25 mol) is added. The mixture is heated to reflux for approximately 3 hours with elimination of the excess $AcONH_4$ supernatant and of the water released by means of a Dean-Stark trap. The reaction mixture is concentrated under reduced pressure, taken up in AcOEt and washed with a saturated solution of $NaHCO_3$ (100 ml) and with a saturated solution of NaCl (100 ml). The AcOEt phase is dried over $Na_2SO_4$, filtered and concentrated under vacuum. The crude product obtained is purified by flash chromatography on silica gel with a $CHCl_3$/MeOH mixture 98/2 as eluant. The fractions containing the pure product are combined and concentrated in order to produce the product (2.52 g; 40%) in the form of a slightly brown foam which is used in the following stage without additional purification.

1.c) 2-(1-(S)-((phenylmethoxy)carbonyl)-amino-2-(cyclohexyl)methyl)-1-((2-ethoy-2-oxo)ethyl)-4-(2-methylphenyl)-imidazole Intermediate 1.b (2.52 g; 6.0 mmol) is solubilized in DMF (20 ml) and treated with $K_2CO_3$ (1.67 g, 12.1 mmol) and ethyl bromoacetate (1.34 ml; 12.5 mmol) is added. The mixture obtained is heated at 45° C. for one and a half hours. The mixture is diluted with ether (50 ml) and washed with a saturated solution of $NaHCO_3$ solution (50 ml) then with a saturated solution of NaCl (50 ml). The ethereal layer is dried over $Na_2SO_4$, filtered and concentrated in order to produce an oil which is used in the following stage without additional purification.

Mass spectrum: 504.3 MH+.

1.d) 8-(cyclohexylmethyl)-6-oxo-2-(2-methylphenyl)-imidazo[1,2-a]pyrazine

The crude intermediate of Stage 1.c is solubilized in acetic acid (50 ml) containing a 10% Pd on carbon catalyst (152 mg), then hydrogenated under a pressure of 50 psi of $H_2$ for 18 hours at ambient temperature. The catalyst is eliminated by filtration and the filtrate is heated at 70° C. for 2 hours. The mixture obtained is concentrated under reduced pressure, dissolved in $CH_2Cl_2$ (100 ml) and washed with a saturated solution of $NaHCO_3$ (100 ml). The $CH_2Cl_2$ layer is dried over $Na_2SO_4$, filtered and concentrated in order to produce a viscous oil which is used in the following stage without additional purification.

Mass spectrum: 324.3 MH+.

1.e) 8-(cyclohexylmethyl)-2-(2-methylphenyl)-4,5,6,7-tetrahydro-imidazo[1,2-a]pyrazine The crude intermediate of Stage 1.c is solubilized in THF (25 ml) and treated at ambient temperature with a 1M solution of BH3 in THF (25 ml) for half an hour then taken to reflux for 1 hour. The mixture is cooled down using an ice bath and 4N HCl (40 ml) is added dropwise at 0° C. The mixture is taken to ambient temperature then taken to reflux for 1 hour. The reaction medium is then cooled down, filtered and concentrated under reduced pressure. The residue is treated with a saturated solution of NaHCO$_3$ (50 ml) and extracted with CH$_2$Cl$_2$ (3×50 ml). The CH$_2$Cl$_2$ phases are dried over Na$_2$SO$_4$, filtered and concentrated in order to produce a slightly brown oil (1.63 g; yield of 87% relative to Stages 1.c, 1.d and 1.e).

Mass spectrum: 310.3 MH+.

1.f) 8-(cyclohexylmethyl)-7-[2-(((1,1-dimethylethoxy) carbonyl)amino)-1-oxo-3-((triphenylmethyl)thio)propyl]-2-(2-methylphenyl)-4,5,6,7-tetrahydro-imidazo-[1.2a]-piperazine Diisopropylcarbodiimide (908 µl; 5.80 mmol) and BocCys(trt)-OH (5.37 g; 11.6 mmol) are solubilized in CH$_2$Cl$_2$ (25 ml), the mixture obtained being agitated for 45 minutes. 8-(cyclohexylmethyl)-2-(2-methylphenyl)-4,5,6,7-tetrahydro-imidazo[1,2-a]pyrazine (1.63 g; 5.27 mmol) is then added. The reaction mixture is agitated overnight at ambient temperature. The solvent is eliminated under reduced pressure and the product obtained is purified by flash chromatography on silica gel with a CH$_2$Cl$_2$/MeOH mixture 98/2 as eluant. The pure fractions are concentrated in order to produce a viscous oil which is which is used in the following stage without additional purification.

Mass spectrum: 755.6 MH+.

1.g) 7-(2-amino-1-oxo-3-(mercaptopropyl))-8-(cyclohexylmethyl)-2-(2-methylphenyl)-4,5,6,7-tetrahydro-imidazo-[1.2a]-piperazine: 1

The intermediate of Stage 1.f (3.54 g; 4.69 mmol) is solubilized in trifluoroacetic acid (TFA, 80 ml) containing triisopropylsilane (1.92 ml; 9.38 mmol) and the reaction mixture is agitated at ambient temperature under nitrogen for one hour. The reaction mixture is filtered and the filtrate is concentrated under reduced pressure. The residue is extracted by trituration with an aqueous solution of TFA at 0.1% (6×65 ml) and filtered. The crude product is purified by preparative HPLC on a C18 column using a gradient of 0 to 20% of CH$_3$CN in an aqueous solution of TFA at 0.1% for 30 minutes. The pure fractions of the product are collected and lyophilized. The initial product is lyophilized twice from a dilute solution of HCl in order to produce the product in the form of its hydrochloride (740 mg; 32%).

Mass spectrum: 413.2 MH+. NMR $^1$H (DMSO-d6): 8.5–9.0 (3H, d, broad); 7.8–8.0 (1H, s); 7.5–7.7 (1H, d); 7.2–7.5 (3H, m); 5.8–6.1 (1H, m); 4.65–4.8 (1H, s); 4.5–4.7 (1H, d); 4.1–4.4 (2H, m); 3.8–4.0 (1H, m); 3.2–3.7 (H$_2$O); 2.8–3.1 (2H, m); 2.35–2.5 (3H, s); 2.0–2.2 (1H, m); 1.8–2.05 (2H, m); 1.25–1.4 (4H, broad s); 1.3–0.9 (6H, m).

Example 2

7-(2-amino-1-oxo-3-thiopropyl)-8-(cyclohexylmethyl)-2-phenyl-5,6,7,8-tetrahydroimidazo[1.2a]pyrazine: 2

Compound 2 is prepared according to diagram 1, Stages b to g, according to a method similar to that of Example 1, 2-bromoacetophenone replacing 2-bromo-2'-methylacetophenone in Stage b.

Mass spectrum: 399.2 MH+. NMR $^1$H (DMSO-d6): 8.5–8.9 (3H, broad d); 8.0–8.2 (1H, s); 7.8–8.0 (2H, d); 7.45–7.56 (2H, t); 7.35–7.5 (1H, t); 5.9–6.05 (1H, broad s); 4.65–4.8 (1H, s); 4.5–4.65 (1H, d); 4.1–4.35 (2H, m); 3.8–4.0 (1H, m); 3.2–3.8 (H$_2$O); 3.25–3.4 (1H, t); 2.8–3.05 (2H, m); 2.05–2.2 (1H, d); 1.85–2.05 (2H, t); 1.55–1.75 (4H, broad s); 1.15–1.3 (1H, broad s); 1.2–0.9 (5H, m).

Example 3

7-(2-amino-1-oxo-3-thiopropyl)-2-(2-methoxyphenyl)-8-(phenylmethoxy)methyl-5,6,7,8-tetrahydroimidazo[1.2a]pyrazine: 3

Compound 3 is prepared according to diagram 1, Stages b to g, according to a method similar to that of Example 1, Boc-(L)-Ser(Bzl)-OH replacing Cbz-(L)-cyclohexylalanine in Stage b and Stage d being replaced by a deprotection using TFA and iPr$_3$SiH according to a method similar to reaction 1.g. The product is obtained in the form of a pair of diastereoisomers in a proportion of 2:3.

Mass spectrum: 453.2 MH+.

The retention times for the diastereoisomers are 6.58 and 7.07 minutes respectively in the following HPLC system:

Eluant: 30–50% CH$_3$CN/0.1% TFA

Duration of elution: 24 minutes

Detection: 254 nm

Column: Vydac protein and C18 peptide

Example 4

7-(2-amino-1-oxo-3-thiopropyl)-2-(2-methoxyphenyl)-8-(1-phenylmethoxy)ethyl-5,6,7,8-tetrahydroimidazo[1.2a]pyrazine: 4

Compound 4 is prepared according to diagram 1, Stages b to g, according to a method similar to that of Example 3, Boc-(L)-Thr(Bzl)-OH replacing Boc-(L)-Ser(Bzl)-OH in Stage b.

Mass spectrum: 467.3 MH+. NMR $^1$H (DMSO-d6): 8.5–8.9 (3H, d, broad); 8.0–8.1 (1H, s); 7.95–8.1 (2H, d); 7.4–7.5 (1H, t); 7.15–7.3 (1H, d); 7.0–7.2 (3H, m); 6.9–7.05 (2H, m); 5.85–5.95 (1H, d); 4.75–4.85 (1H, broad s); 4.65–4.8 (1H, broad s); 4.35–4.65 (3H, m); 4.1–4.25 (2H, q); 3.9–4.0 (3H, s); 2.8–3.1 (2H, m); 1.2–1.4 (3H, d).

Example 5

7-(2-amino-1-oxo-3-thiopropyl)-2-(2-methoxyphenyl)-8-(phenoxyethyl)-5,6,7,8-tetrahydroimidazo[1.2a]pyrazine: 5

Compound 5 was prepared according to the following synthesis diagram:

Diagram 2

5.h) 2-(1-(S)-((phenylmethoxy)carbonyl)-amino-2-(2-oxo-2-(phenylmethoxy)ethyl)-4-(2-methoxyphenyl)-imidazole Cbz-(L)-Asp(Obzl)-OH (5.00 g; 14.0 mmol) and $Cs_2CO_3$ (2.28 g; 7.00 mmol) are mixed in a 1:1 mixture of $DMF:H_2O$ (75 ml). The mixture obtained is agitated until it becomes homogenous. The solvents are eliminated under reduced pressure, the residue is dissolved in DMF (60 ml) and 2-bromo-2'-methoxyacetophenone (3.21 g; 14.0 mmol) in DMF (30 ml) is added. The mixture obtained is agitated for half an hour at ambient temperature then filtered and concentrated under reduced pressure. The keto-ester obtained is triturated with a 1:1 mixture of $Et_2O$:hexanes (2×40 ml) then suspended in xylenes (100 ml). Ammonium acetate (17.5 g; 0.23 mol) is added and the mixture is heated at reflux for approximately one hour and 30 minutes with elimination of the excess $AcONH_4$ and of the water released by means of a Dean-Stark trap. The reaction medium is washed with a saturated solution of $NaHCO_3$ (50 ml), dried over $Na_2SO_4$, filtered and concentrated under vacuum in order to produce 6.66 g (98%) of desired product.

Mass spectrum: 486.3 (MH+).

5.i) 2-(1-(S)-((phenylmethoxy)carbonyl)-amino-2-((2-phenylmethoxy-2-oxo)ethyl)-1-((2-ethoxy-2-oxo)ethyl)-4-(2-methoxyphenyl)-imidazole Intermediate 5.i is prepared according to a method similar to that of Stage 1.c.

Mass spectrum: 572.3 MH+.

5.j) (6-oxo-2-(2-methoxyphenyl)-5,6,7,8-tetrahydro-imidazo[1,2-a]pyrazin-8-yl)-acetic acid Intermediate 5.j is prepared according to a method similar to that of Stage 1.d.

Mass spectrum: 302.2 MH+. NMR $^1$H (DMSO-d6): 8.35–8.5 (1H, d, broad); 8.0–8.1 (1H, dd); 7.45–7.55 (1H, s); 7.15–7.25 (1H, m); 7.0–7.1 (1H, m); 6.9–7.0 (1H, m); 4.85–5.0 (1H, broad s); 4.55–4.75 (2H, q); 3.85–3.95 (3H, s); 2.8–2.95 (2H, d).

5.k) 8-hydroxyethyl-2-(2-methoxyphenyl)-5,6,7,8-tetrahydro-imidazo[1,2-a]pyrazine Intermediate 5.k is prepared according to a method similar to that of Stage 1.e, except for the fact that a molar proportion of 6/9 of $BH_3$ relative to the substrate is used.

Mass spectrum: 274.3 MH+.

5.l) 7-((1,1-dimethylethoxy)carbonyl)-8-hydroxyethyl-2-(2-methyoxyphenyl)-5,6,7,8-tetrahydro-imidazo[1,2-a]pyrazine Intermediate 5.k (1.36 g; 5.0 mmol) is suspended in $H_2O$ (5 ml) and a mixture of di-t-butyldicarbonate (1.20 g; 5.5 mmol) in p-dioxane (10 ml) is added. The reaction medium is agitated vigorously and maintained at pH 8.0–8.4 by the dropwise addition of a 2.5N solution of NaOH until the reaction finishes (monitoring of the reaction by TLC on silica gel, eluant AcOEt:hexanes 3:2). The crude product is purified by flash chromatography on silica gel with an AcOEt:hexanes mixture 3:2 as eluant (Biotage system, pre-filled columns 4×15 cm). The fractions containing the product are combined and concentrated under vacuum in order to produce a white foam (1.60 g; 86%).

Mass spectrum: 374.3 MH+. NMR $^1$H (DMSO-d6): 7.95–8.05 (1H, d,d); 7.45–7.55 (1H, s); 7.10–7.25 (1H, m); 7.0–7.1 (1H, m); 6.9–7.05 (1H, m); 5.05–5.15 (1H, t); 4.25–4.35 (1H, t); 4.05–4.2 (1H, broad s); 4.0–4.1 (1H m); 3.9–4.0 (3H, s); 3.9–4.0 (1H, m); 3.25–3.35 (2H, m); 1.9–2.1 (2H, m); 1.15–1.25 (9H, s).

5.m) 7-((1,1-dimethylethoxy)carbonyl)-8-phenoxyethyl-2-(2-methoxyphenyl)-5,6,7,8-tetrahydro-imidazo[1,2-a]pyrazine Intermediate 5.l (746 mg; 2.00 mmol) is dissolved in THF (10 ml) containing triphenylphosphine (550 mg; 2.1 mmol) and phenol (198 mg; 2.1 mmol). The mixture is cooled down to 0° C. under nitrogen and diethylazodicarboxylate (330 µl; 2.1 mmol) is added dropwise over 10 minutes. The reaction mixture is then agitated for 2 hours at ambient temperature. The reaction medium is then cooled down again to 0° C. and triphenylphosphine (275 mg; 1.05 mmol) and phenol (99 mg; 1.05 mmol) are added. Then diethylazodicarboxylate (166 µl; 1.05 mmol) is added dropwise over 10 minutes then the mixture is agitated again for 1 hour at ambient temperature. The solvents are eliminated under reduced pressure and the crude product is purified by flash chromatography on silica gel with an AcOEt:hexanes mixture 3:2 as eluant. The fractions containing the product are combined and concentrated under vacuum. After recrystallization from AcOEt and hexanes, the desired product is obtained in the form of a white solid (863 mg; 96%).

Mass spectrum: 450.4 MH+.

5.n) 7-(2-(((1,1-dimethylethoxy)carbonyl)amino)-1-oxo-3-((triphenylmethyl)thio)propyl)-2-(2-methoxyphenyl)-8-(phenoxyethyl)-4,5,6,7-tetrahydro-imidazo-[1.2a]-piperazine Intermediate 5.m (850 mg; 1.89 mmol) is treated with a mixture of TFA (10 ml) containing iPr$_3$SiH (387 µl, 1.89 mmol) at ambient temperature for 20 min. The solvents are eliminated under reduced pressure and the crude product is divided between AcOEt (15 ml) and a saturated solution of NaHCO$_3$ (15 ml). The AcOEt phase is dried over Na$_2$SO$_4$, filtered and concentrated under reduced pressure. The deprotected product is coupled to Boc-(L)-Cys(Trt)-OH according to a method similar to that of Stage 1.f (1.26 g; 84%).

5.o) 7-(2-amino-1-oxo-3-thiopropyl)-2-(2-methoxyphenyl)-8-(phenoxyethyl)-4,5,6,7-tetrahydro-imidazo-[1.2a]-piperazine Product 5 is prepared starting from intermediate 5.n according to a method similar to that of Stage 1.g.

Mass spectrum: 274.3 MH+. NMR $^1$H (DMSO-d6 at 90° C.): 8.5–9.2 (3H, s, broad); 7.95–8.1 (1H, d); 7.85–8.0 (1H, s); 7.35–7.5 ($^1$H, m); 7.15–7.35 (3H, m); 7.0–7.15 (1H, t); 6.85–7.0 (3H, m); 5.9–6.1 (1H, s, broad); 4.5–4.8 (2H, m, broad); 4.15–4.45 (3H, m, broad); 3.9–4.0 (3H, s); 3.75–4.0 (1H, m, broad); 2.8–3.05 (2H, m, broad); 2.55–2.75 (2H, m, broad).

Example 6

7-(2-amino-1-oxo-3-thiopropyl)-2-(2-methoxyphenyl)-8-(phenoxyethyl)-5,6,7,8-tetrahydro-imidazo[1.2a]pyrazine, dimer: 6

Compound 5.o (467 mg; 0.687 mmol) is solubilized in H$_2$O (25 ml) and the pH of the solution is adjusted to 7.2 by adding a dilute aqueous solution of NH$_4$OH. Acetonitrile is added in order to produce a limpid solution and the mixture is agitated at ambient temperature overnight. The crude product is purified by preparative HPLC on a C18 column using a gradient of 15 to 40% CH$_3$CN in TFA at 0.1% over a period of 50 minutes. The pure fractions of product are collected and lyophilized. The initial product is lyophilized twice from a dilute solution of HCl in order to produce the product in the form of its hydrochloride (161 mg; 45%).

Mass spectrum: 903.5 MH+. NMR $^1$H (DMSO-d6 at 90° C.): 8.7–9.3 (3H, broad s); 7.95–8.1 (1H, d); 7.85–8.0 (1H, s); 7.3–7.5 (1H, t); 7.1–7.3 (3H, m); 7.0–7.15 (1H, t); 6.8–7.0 (3H, m); 5.85–6.1 (1H, broad s); 4.7–4.9 (1H, broad s); 4.45–4.7 (1H, broad m); 4.1–4.5 (4H, broad m); 3.85–4.0 (4H, s); 3.3–3.5 (2H, broad m); 2.5–2.8 (2H, broad m).

Example 7

7-(2-amino-1-oxo-3-thiopropyl)-2-(2-methoxyphenyl)-8-(phenylsulphonylethyl)-5,6,7,8-tetrahydro-imidazo[1.2a]pyrazine: 7

Compound 7 was prepared according to the synthesis diagram below:

Diagram 3

-continued 7.p) 7-((1,1-dimethylethoxy)carbonyl)-2-(2-methoxyphenyl)-8-(phenylthioethyl)-5,6,7,8-tetrahydro-imidazo[1,2-a]pyrazine Intermediate 5.1 (1.23 g; 3.30 mmol), tri-n-butylphosphine (1.64 ml; 6.60 mmol) and phenyldisulphide (1.44 g; 6.60 mmol) are mixed in THF (10 ml). The mixture is agitated at ambient temperature under argon for 4 hours. The solvents are eliminated under reduced pressure and the crude product is purified by flash chromatography on silica gel with an AcOEt:hexanes mixture 1:1 as eluant. The fractions containing the product are combined and concentrated under vacuum in order to produce the product in the form of a white foam (1.43 g; 93%).

Mass spectrum: 466.3 MH+.

7.q) 7-((1,1-dimethylethoxy)carbonyl)-2-(2-methoxyphenyl)-8-(phenylsulphonylethyl)-5,6,7,8-tetrahydro-imidazo[1,2-a]pyrazine Intermediate 7.p (650 mg; 1.40 mmol) is dissolved in $CH_2Cl_2$ (10 ml) and 3-chloroperoxybenzoic acid (483 mg; 2.80 mmol) is added in several portions over a period of 10 minutes. The mixture is poured onto a silica column and eluted with a hexanes:AcOEt mixture 7:3, then a hexanes:AcOEt mixture 1:1 in order to produce the pure product (220 mg; 32%).

Mass spectrum: 498.3 MH+. NMR $^1$H (DMSO-d6 at 30° C.): 7.9–8.0 (3H, m); 7.7–7.85 (1H, m); 7.6–7.75 (2H, m); 7.45–7.55 (1H,s); 7.15–7.25 (1H, m); 6.9–7.1 (2H, m); 5.1–5.25 (1H, t); 4.1–4.3 (1H, broad d); 4.0–4.15 (1H, m); 3.8–4.0 (1H, m); 3.85–3.95 (3H, s); 3.6–3.8 (1H, m); 3.4–3.6 (1H, m); 3.2–3.4 ($H_2O$ plus a blurred signal); 1.9–2.3 (2H, m); 1.3–1.5 (9H, s).

Stage 7.n)

Stage 7.n is carried out according to a method similar to Stage 5.n. The crude product is used without further purification in the following stage.

Stage 7.o)

The stage 7.o is carried out according to a method similar to Stage 5.o.

Mass spectrum: 501.3 MH+.

Preparation of the Compound of Formula (VII)

This compound, which is close to those described in Patent Application PCT WO 97/30053, can be prepared according to the following synthesis diagram:

-continued

4) [O] (cyclization)
5) deprotection

1) BOC-Cys or BOC-Pen/EDC/HOBT
2) H+
3) BOC-Cys ou BOC-Pen/EDC/HOBT
4) [O] (cyclization)
5) deprotection 1) BOC-Cys or BOC-Pen/EDC/HOBT
2) deprotection
3) BOC-Cys-al/Na(OAc)$_3$BH
4) [O] (cyclization)
5) deprotection R' = H or $CH_3$;
Cys = Cysteine, Cys-al = Cysteinal;
Pen = Penicillamine, Pen-al = Penicillaminylal Pharmacological Part

In order to illustrate the usefulness of the invention, there follows a study on the effect of the treatment of a human MCF-7 cell line with the following compounds:

bis-1,1'-[7-(2-amino-1-oxo-3-thiopropyl)-8-(cyclohexylmethyl)-2-(2-methoxyphenyl)-5,6,7,8-tetrahydroimidazo[1.2a]pyrazine disulphide, designated in this part as compound (I);

bis-1,1'-7-(2-amino-1-oxo-3-thiopropyl-(2-(1-naphthyl)-8-(2-methylpropyl)-5,6,7,8-tetrahydroimidazo[1.2a]pyrazin-7-yl), designated in this part as compound (II);

7-(2-amino-1-oxo-3-thiopropyl)-8-(cyclohexylmethyl)-2-(2-methylphenyl)-5,6,7,8-tetrahydroimidazo[1.2a]pyrazine, designated in this part as compound (III);

the compound of formula:

designated in this part as compound (IV);
7-(2-amino-1-oxo-3-thiopropyl)-8-butyl-2-(2-methoxyphenyl)-5,6,7,8-tetrahydroimidazo[1.2a]pyrazine, designated in this part as compound (V);
bis-1,1'-[7-(2-amino-1-oxo-3-thiopropyl)-2-(methoxyphenyl)-8-(1-methylpropyl)-5,6,7,8-tetrahydroimidazo[1.2a]pyrazine], designated in this part as compound (VI);
the compound of formula:

designated in this part as compound (VII).

Procedures

Cell Line

The MCF-7 cell lines (human pleural cells, breast cancer) were acquired from the American Tissue Culture Collection (Rockville, Md., USA).

Measurement of the Intracellular Quantity of Cyclic AMP for the MCF-7 Cells

MCF-7 cells ($2.10^4$ cells/well) seeded in 24-well plates are cultured for 5 days in Dulbecco's modified Eagle medium (Gibco-Brl, Cergy-Pontoise, France) completed with 10% of foetal calf serum inactivated by heating (Gibco-Brl, Cergy-Pontoise, France ), 50000 units/l of penicillin and 50 mg/l streptomycin (Gibco-Brl, Cergy-Pontoise, France), and 2 mM of glutamin (Gibco-Brl, Cergy-Pontoise, France). The culture medium is replaced after two washes with a medium without a serum completed or uncompleted with the specified agents for a time indicated in the different figures. Agents activating the production of cyclic AMP are then added at 37° C. The reaction is stopped after 30 minutes by suppressing the medium and rapidly adding 100 µl of a 0.1N solution of HCl. These extracts are frozen at −80° C. until they are used. The concentration of cAMP is measured using a commercial measurement kit (reference NEK033 from NEN, Les Ulis, France), following the manufacturer's instructions. The radioactivity is determined by a Gamma counter (Gamma Master-1277, LKB, Turku, Finland).

Measurement of in vitro Cell Proliferation

The MCF-7 cells (3000 cells/well) are cultured in 96-well plates in 80 µl of Dulbecco's modified Eagle medium (Gibco-Brl, Cergy-Pontoise, France) completed with 10% of foetal calf serum inactivated by heating (Gibco-Brl, Cergy-Pontoise, France), 50000 units/l of penicillin and 50 mg/l streptomycin (Gibco-Brl, Cergy-Pontoise, France), and 2 mM of glutamin (Gibco-Brl, Cergy-Pontoise, France) were seeded on a 96-well plate on day 0. The cells were treated on day 1 for 96 hours with increasing concentrations of up to 50 µM of each of the compounds to be tested. After this period, quantification of cell proliferation is determined by a colorimetric test, based on the cleavage of the WST1 tetrazolum salt by the mitochondrial dehydrogenases in the viable cells, leading to the formation of formazan (Boehringer Mannheim, Meylan, France). These tests are carried out in duplicate with 8 determinations per concentration tested. For each compound to be tested, the values included in the linear part of the sigmoid were retained for linear regression analysis and used to estimate the inhibitory concentration ($IC_{50}$).

Measurement of the MAP Kinase Activity

MCF7 cells (5.105 cells/well) are cultured in 6 wells in Dulbecco's modified Eagle medium (Gibco-Brl, Cergy-Pontoise, France) completed with 10% of foetal calf serum inactivated by heat (Gibco-Brl, Cergy-Pontoise, France), a mixture of antibiotics: 50000 units/l of penicillin and 50 mg/l of streptomycin (Gibco-Brl, Cergy-Pontoise, France) and 2 mM of glutamin (Gibco-Brl, Cergy-Pontoise, France). After 24 hours of culture, the cells are incubated for 48 hours in medium containing no serum in order to return the cells to a state of rest. The cells are then treated for 1 hour either with compound I or with PD98059 (Calbiochem, France Biochem, Meudon, France), a specific inhibitor of MAP kinase activation. The cells are then stimulated (or not) for 5 minutes with 12.5 ng/ml of epidermal growth factor (EGF). The reaction is stopped by two washes with PBS (Gibco-Brl, Cergy-Pontoise, France), at 4° C. containing neither calcium nor magnesium and by adding 150 µl of lysis buffer at 4° C. the composition of which is the following: 10 mM of tris, 150 mM of NaCl, 2 mM of EGTA, 2 mM of dithiothreitol, 1 mM of PMSF, 2 mM of orthovanadate, 10 µg/ml of leupeptin and 10 µg/ml of aprotinin. Measurement of the proteins contained in the extracts is carried out by Bradford's method (Biorad reagents, Ivry-Sur-Seine, France). These extracts are frozen at −80° C. until they are used. The activity of the MAP kinase is measured using a commercial measurement kit (reference RPN 84, Amersham Life Science, Les Ulis, France) following the manufacturer's instructions. The radioactivity is determined using a Packard scintillation counter (Tricarb 5000CA).

Equipment

The vasoactive intestinal peptide (VIP) was acquired from Bachem (Voisins le Bretonneux, France). The choleric toxin, forskolin, isoproterenol, prostaglandin E2 and PD 98059 were acquired from Calbiochem (France Biochem, Meudon, France). The compounds of formulae (I), (II), (III), (IV), (V), (VI) and (VII) were supplied by Biomeasure Inc. (Milford, Mass., USA). All these compounds were used following their manufacturers' recommendations.

Results

Figure 1:
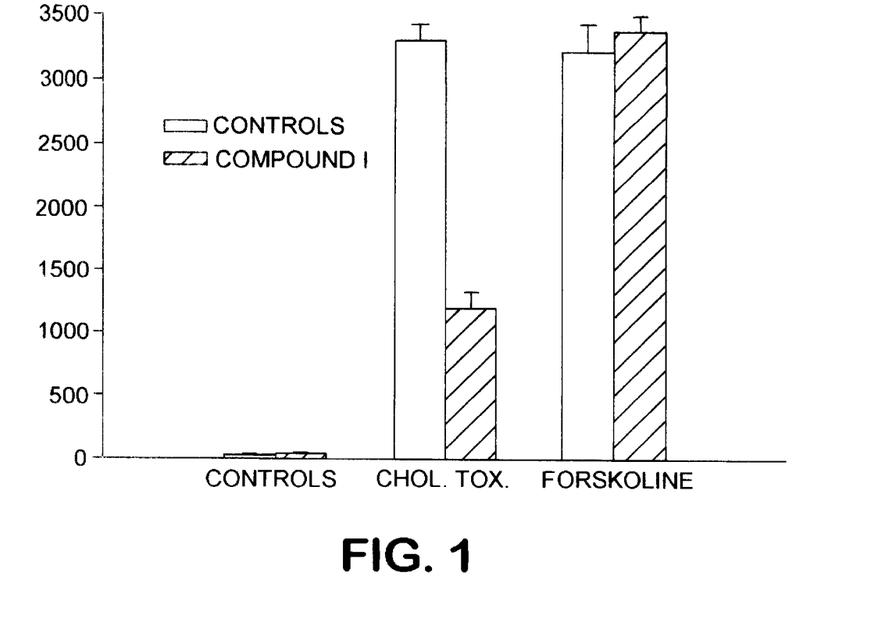
FIG. 1 is a bar graph of the activation of adenylate cyclase by cholera toxin and forskolin.

FIG. 1 shows that activation of the adenylate cyclase by the choleric toxin (200 ng/ml) or by forskolin (10 µM) leads to a very significant increase in the cyclic AMP level. Pretreatment of the cells for 30 minutes with 30 µM of comound (I) does not modify the production of cyclic AMP induced by the direct activator of the adenylate cyclase, forskolin. On the other hand, the production of cyclic AMP stimulated by the direct activator of the sub-unit, the choleric toxin, is greatly inhibited by compound (I). This shows that the adenylate cyclase itself is not modified by compound (I) and that the latter prevents the formation of the heterotrimeric complex.

Figure 2:
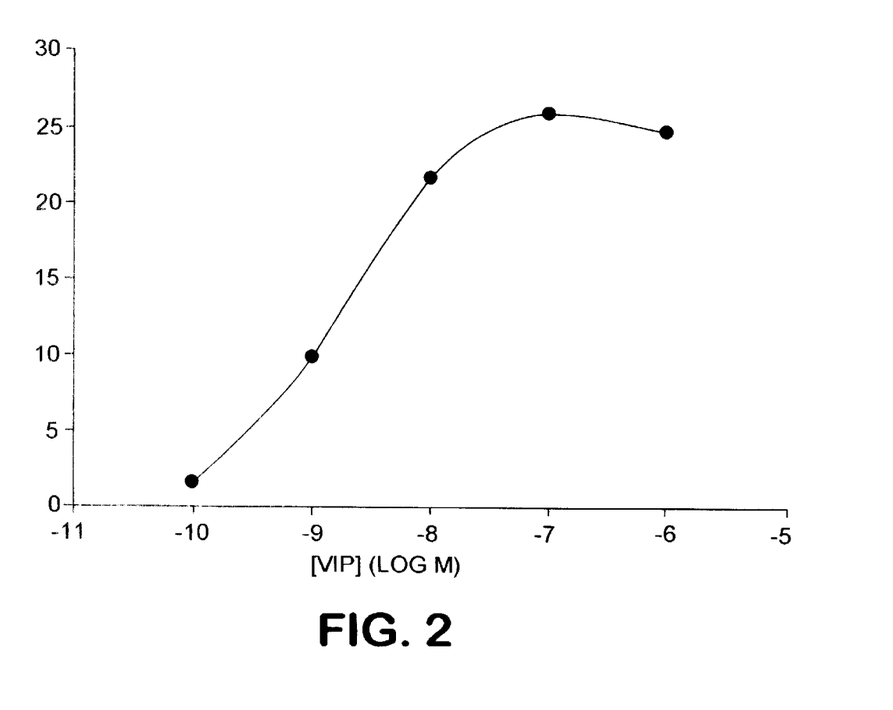
FIG. 2 is a graph of the treatment of human breast cancer cells with VIP.

VIP has been presented as an extra-cellular ligand of a receptor coupled with the G protein which stimulates the synthesis of cyclic AMP in human breast cancer cells. FIG. 2 shows that treatment with VIP of MCF-7 human breast cancer cells increases the intracellular quantity of cyclic AMP in a concentration-dependent manner. A VIP concentration of 10 nM which offers a quasi-optimum production of cyclic AMP is used for the following tests. This concentration agrees with the data already published relating to the T47D human breast cancer cell line.

Figure 3:
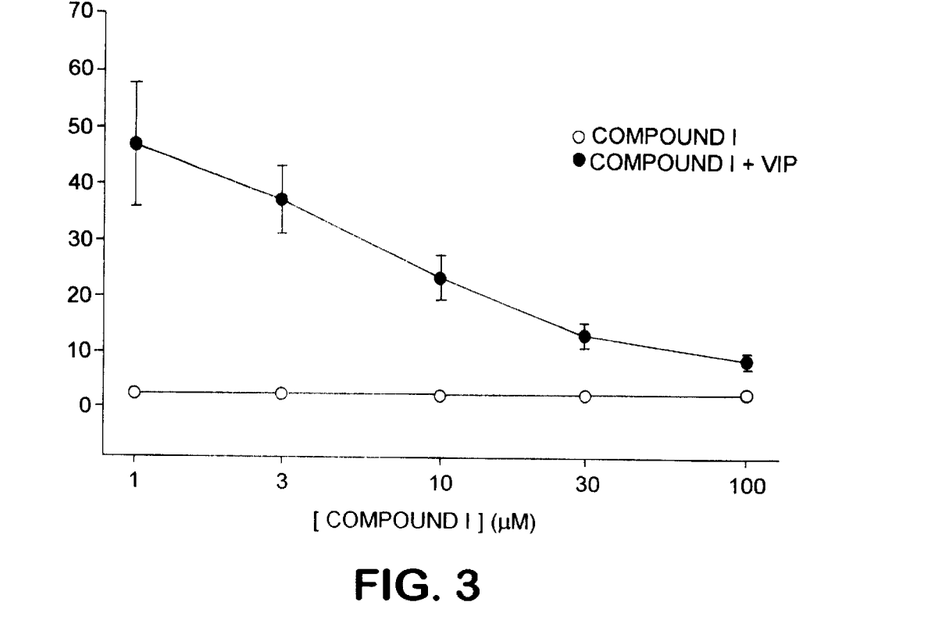
FIG. 3 is a graph of the treatment of human breast cell with a compound of Formula I alone and with VIP.

FIG. 3 shows that a 30-minute pretreatment of the MCF-7 cells resulting from the in vitro cultures with the compound of formula (I) is sufficient to inhibit the accumulation of cyclic AMP cyclic stimulated by VIP in a concentration-dependent manner. An almost complete inhibition was obtained at a concentration of 100 μM of the compound of formula (I). These results show that a treatment with compound (I) is sufficient to block the transduction of the signal the route of which uses the heterotrimeric G proteins as mediators.

Figure 4:
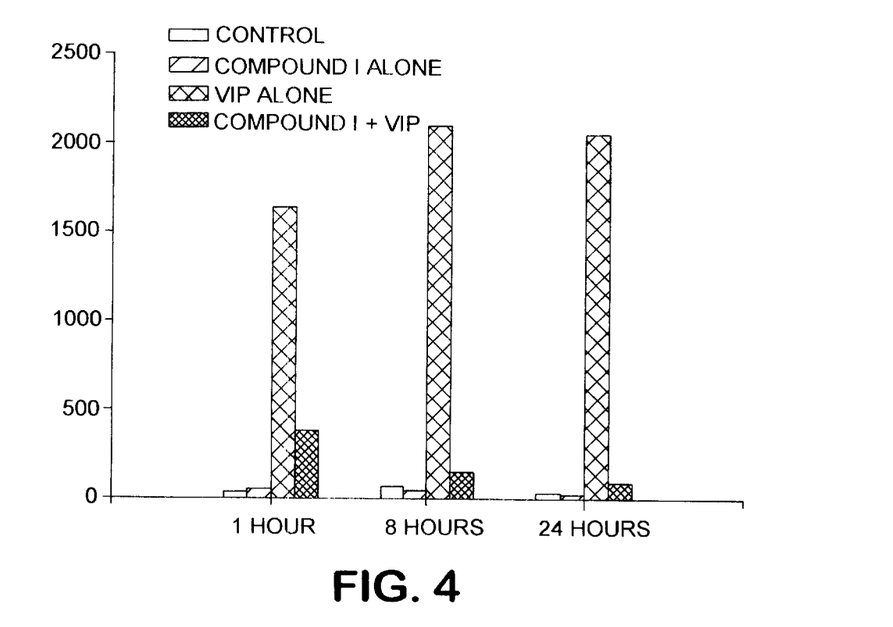
FIG. 4 is a bar graph of inhibitors of cyclic AMP with a compound of Formula I, with VIP and with a combination thereof.
Figure 5:
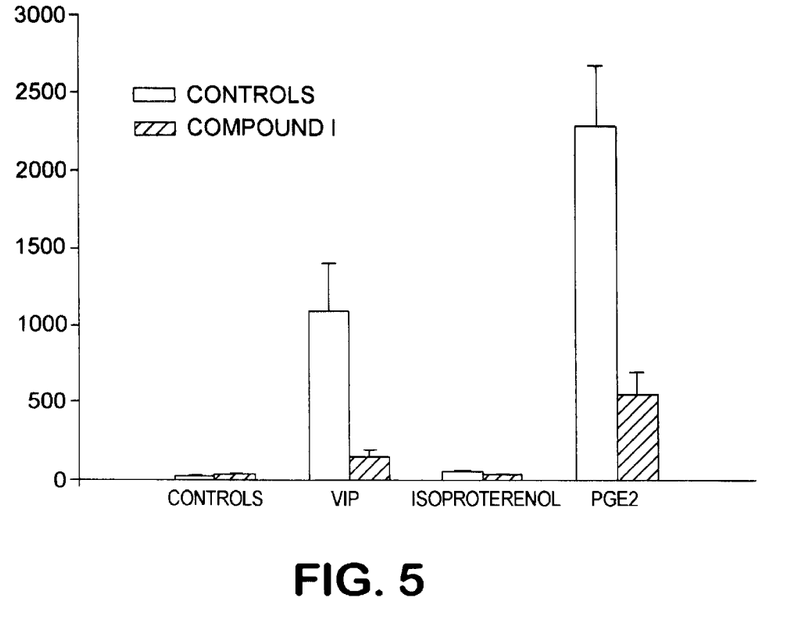
FIG. 5 is a bar graph of treatment with isoproterenol and PGE2.

FIG. 4 shows that a treatment for an hour with the compound of formula (I) is sufficient to modify the response to VIP. Treatments of a longer duration (8 hours and 24 hours) continue to inhibit the production of cyclic AMP but the main effect is obtained very rapidly.

Compound (I) is also capable of inhibiting the formation of cyclic AMP induced by other agents which stimulate the receptors with seven transmembrane domains. In MCF7 cells, for example, the activity of the adenylate cyclase greatly increased by the prostaglandin $E_2$ is inhibited by a treatment for 30 minutes with compound (I). This suggests that treatment of the cells with compound (I) modifies the heterotrimeric form of the G proteins by disassociating the sub-unit of the β/γ dimer.

Inhibition of stimulation by VIP is not restricted to compounds of a structure analogous to that of the compound of formula (I). As shown in Table I, compounds (II), (III), (IV), (V), (VI) and (VII) tested in the same model are also capable of reducing the quantity of cyclic AMP induced by VIP.

All these results suggest that the compounds tested modulate the activity of the adenylate cyclase by modifying the heterotrimeric form of the G proteins. Now, it is known that the β/γ dimers can directly activate effectors leading to the activation of kinases regulated by extracellular signals (ERK's) or MAP kinases.

Figure 6:
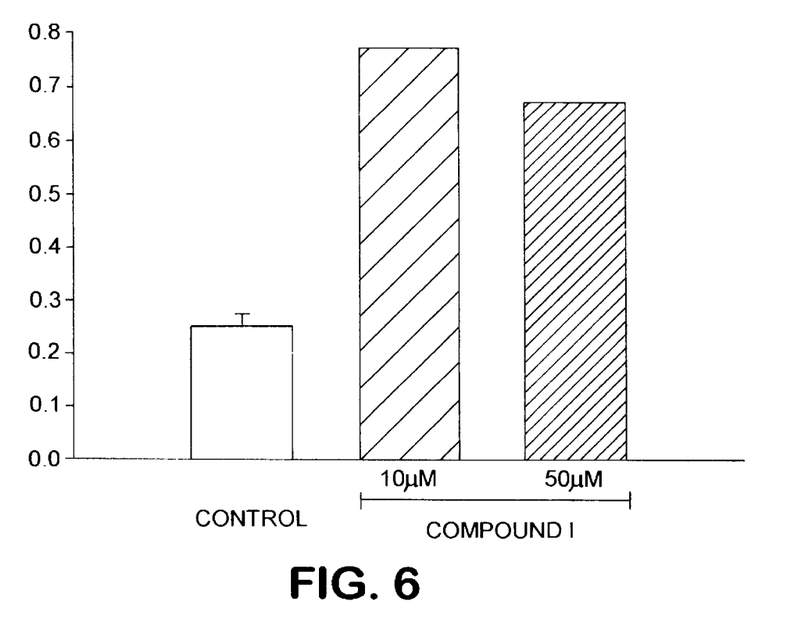
FIG. 6 is a bar graph of treatment of human breast cancer cells with compound I.
Figure 7:
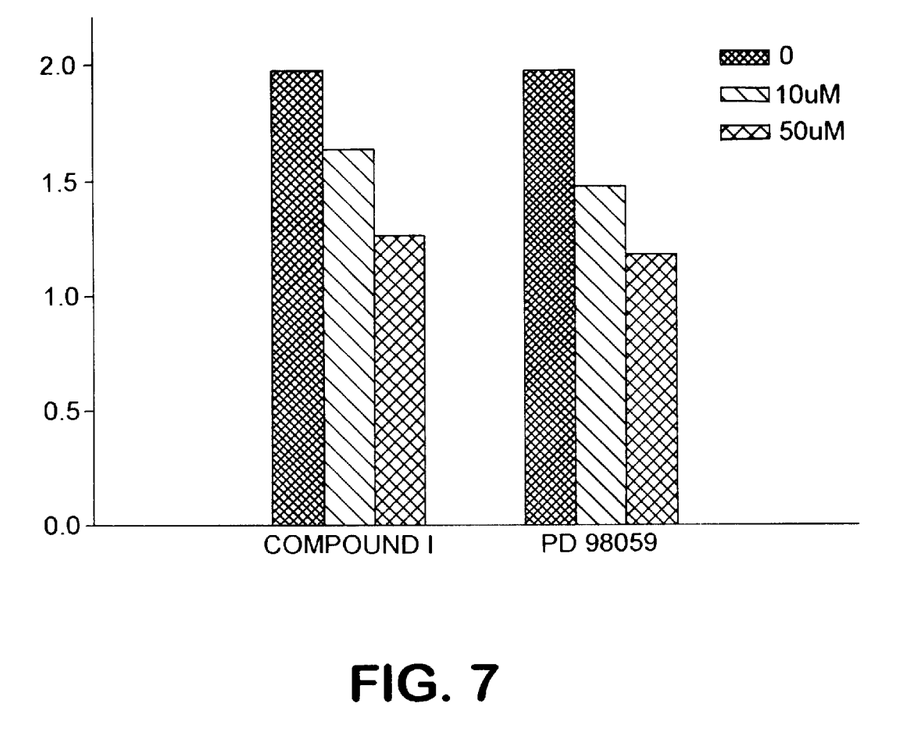
FIG. 7 is a bar graph of treatment of human breast cancer with a compound of Formula I or PD 98059.

FIG. 6 shows that treatment of the cells for 1 hour with compound (I) doubles the basal activity of the MAP kinase. This suggests that by preventing the formation of the heterotrimeric complex, compound (I) releases the heterodimer—which itself remains linked to the membrane and activates the ras route. On the other hand, FIG. 7 shows that after stimulation of the MAP kinase by the growth factor EGF for 5 minutes, the activity of the enzyme is increased by approximately 7 times. Pretreatment of the cells for 1 hour either with compound (I) or with PD98059, a specific inhibitor of MAP kinase activation, halves the activity of the MAP kinase. These results suggest that compound (I) stimulates the basal state of the ras route and inhibits this same route if it is stimulated, thus explainining its antiproliferative effect. Table II in fact shows that compounds (I), (II), (III) and (IV) are capable of inhibiting the in vitro proliferation of MCF7 human tumour cells.

TABLE I

| Compound | Inhibition at 30 μM |
|---|---|
| (I) | 86% |
| (II) | 71% |
| (III) | 59% |
| (IV) | 52% |
| (V) | 68% |
| (VI) | 52% |
| (VII) | 65% |

Effects of Compounds I, II, III and IV Incubated for 30 Minutes on the Production of Cyclic AMP Stimulated by VIP in MCF7 Cells The cells are incubated for 30 minutes in the presence or not of compounds I, II, III and IV (30 μM) which are then stimulated by $10^{-8}$ M of VIP. The quantification of cyclic AMP is determined by radioimmunoassay. The data represents the average±MSD (n=5 for the control and n=1 for the different compounds).

TABLE II

| Compound tested | $IC_{50}$ (μM) |
|---|---|
| compound I | 9.4 |
| compound II | 15.0 |
| compound III | 16.1 |
| compound IV | 34.6 |

Inhibition of the in vitro Growth of MCF7 Cells by Compounds I, II, III and IV

The results of the $IC_{50}$ are expressed in μM and represent the average of 2 experiments.

What is claimed is:

1. A compound chosen from the group consisting of:

7-(2-amino-1-oxo-3-thiopropyl)-8-(cyclohexylmethyl)-2-(methylphenyl)-5,6,7,8-tetrahydroimidazo[1.2a]pyrazine;

7-(2-amino-1-oxo-3-thiopropyl)-2-(2-methoxyphenyl)-8-(phenylmethoxy)methyl-5,6,7,8-tetrahydroimidazo[1.2a]pyrazine;

7-(2-amino-1-oxo-3-thiopropyl)-2-(2-methoxyphenyl)-8-(1-phenylmethoxy)ethyl-5,6,7,8-tetrahydroimidazo[1.2a]pyrazine;

and -7-(2-amino-1-oxo-3-thiopropyl)-2-(2-methoxyphenyl)-8-(phenylsulphonylethyl)-5,6,7,8-tetrahydroimidazo[1.2a]pyrazine.

2. A composition for treating obesity comprising an anti-obesity amount of a compound of formula

A1

$R_1$ is selected from the group consisting of hydrogen, lower alkyl and lower alkylthio, $R_2$ and $R_3$ are individually hydrogen or lower alkyl

$R_4$ is or =O, $R_5$ is selected from the group consisting of a) hydrogen and b) lower alkyl, lower alkenyl, lower alkynyl, aryl, aryl lower alkyl, heterocycle and heterocycle lower alkyl, all unsubstituted or substituted with a member selected from the group consisting of lower alkyl, —O—$R_{10}$, —S(O)$_m$—$R_{10}$,

—N—C(O)—$R_{10}$, —NH—(SO$_2$)—$R_{10}$, —COOR$_{10}$, and m is an integer from 0 to 2, $R_6$ and $R_7$ are individually selected from the group consisting of a) hydrogen, b) unsubstituted and c) lower alkyl, aryl, aryl lower alkyl, heterocycle and heterocycle lower alkyl, all substituted or unsubstituted with a member of the group consisting of —OH, halogen lower alkyl, lower alkoxy,

—COOH and or taken together with the carbon atoms to which they are attached to form aryl or heterocycle, $R_8$ and $R_9$ are individually selected from the group consisting of a) hydrogen and b) lower alkyl, aryl, aryl lower alkyl, heterocycle and heterocycle alkyl, all unsubstituted or substituted with a member of then group consisting of —OH, halogen, lower alkyl, lower alkoxy, —COOH and or taken together with the carbons to which they are attached form aryl or heterocycle, $R_{10}$ and $R_{11}$ are individually selected from the group consisting of hydrogen, lower alkyl, aryl, aryl lower alkyl, heterocycle and heterocycle lower alkyl, $R_{12}$ is selected from the group consisting of —NR$_9$—, —O— and —S—, $R_{13}$ is unsubstituted lower alkyl or lower alkyl substituted with a member selected from the group consisting of lower alkyl, —OR$_{10}$, —S(O)$_m$ and $R_{14}$ is hydrogen or lower alkyl, it being understood that $A_1$ can be a dimer when two $R_1$ are hydrogen and its non-toxic, pharmaceutically acceptable salts sufficient to treat obesity and an inert pharmaceutical carrier.

3. A method of treating obesity in a mammal comprising administering to a mammal in need thereof an amount of a compound of the formula

A1

$R_1$ is selected from the group consisting of hydrogen, lower alkyl and lower alkylthio, $R_2$ and $R_3$ are individually hydrogen or lower alkyl, or =O, $R_5$ is selected from the group consisting of a) hydrogen and b) lower alkyl, lower alkenyl, lower alkynyl, aryl, aryl lower alkyl, heterocycle and heterocycle lower alkyl, all unsubstituted or substituted with a member selected from the group consisting of lower alkyl, —O—$R_{10}$, —S(O)$_m$—$R_{10}$,

—N—C(O)—$R_{10}$, —NH—($SO_2$)—$R_{10}$, —COO$R_{10}$, and m is an integer from 0 to 2, $R_6$ and $R_7$ are individually selected from the group consisting of a) hydrogen b) unsubstituted and c) lower alkyl, aryl, aryl lower alkyl, heterocycle and heterocycle lower alkyl, all substituted or unsubstituted with a member of the group consisting of —OH, halogen, lower alkyl, lower alkoxy,

—COOH and or taken together with the carbon atoms to which they are attached to form aryl or heterocycle, $R_8$ and $R_9$ are individually selected from the group consisting of a) hydrogen and b) lower alkyl, aryl, aryl lower alkyl, heterocycle and heterocycle alkyl, all unsubstituted or substituted with a member of then group consisting of —OH, halogen, lower alkyl, lower alkoxy, —COOH and or taken together with the carbons to which they are attached form aryl or heterocycle, $R_{10}$ and $R_{11}$ are individually selected from the group consisting of hydrogen, lower alkyl, aryl, aryl lower alkyl, heterocycle and heterocycle lower alkyl, $R_{12}$ is selected from the group consisting of —$NR_9$—, —O— and —S—, $R_{13}$ is unsubstituted lower alkyl or lower alkyl substituted with a member selected from the group consisting of lower alkyl, —$OR_{10}$, —$S(O)_m$ and $R_{14}$ is hydrogen or lower alkyl, it being understood that $A_1$ can be a dimer when two $R_1$ are hydrogen and its non-toxic, pharmaceutically acceptable salts sufficient to treat obesity.

4. A method of treating obesity in a mammal comprising administering to a mammal in need thereof an amount of a compound of claim 1 sufficient to treat obesity.

5. The method of claim 3 wherein the compound is selected from the group consisting of
7-(2-amino-1-oxo-3-thiopropyl)-8-(cyclohexylmethyl)-2-(2-methylphenyl)-5,6,7,8-tetrahydroimidazol[1,2a]pyrazine;
7-(2-amino-1-oxo-3-thiopropyl)-8-(cyclohexylmethyl)-2-phenyl)-5,6,7,8-tetrahydroimidazol[1,2a]pyrazine;
7-(2-amino-1-oxo-3-thiopropyl)-2-(2-methoxyphenyl)-8-(phenylmethoxy)methyl-5,6,7,8-tetrahydroimidazol[1,2a]pyrazine;
7-(2-amino-1-oxo-3-thiopropyl)-2-(2-methoxyphenyl)-8-(1-phenylmethoxy)ethyl-5,6,7,8-tetrahydroimidazol[1,2a]pyrazine;
7-(2-amino-1-oxo-3-thiopropyl)-2-(2-methoxyphenyl)-8-(phenoxyethyl)-5,6,7,8-tetrahydroimidazol[1,2a]pyrazine;
7-(2-amino-1-oxo-3-thiopropyl)-2-(2-methoxyphenyl)-8-(phenoxyethyl)-5,6,7,8-tetrahydroimidazol[1,2a]pyrazine, or its dimeric form;
and 7-(2-amino-1-oxo-3-thiopropyl)-2-(2-methoxyphenyl)-8-(phenylsulphonylethyl)-5,6,7,8-tetrahydroimidazol[1,2a]pyrazine.

6. The method of claim 3 wherein the compound is 7-(2-amino-1-oxo-3-thiopropyl)-8-(cyclohexylmethyl)-2-phenyl-5,6,7,8,-tetrahydroimidazol[1,2a]pyrazine.

* * * * *